United States Patent [19]

Dunn et al.

[11] Patent Number: 4,655,777

[45] Date of Patent: Apr. 7, 1987

[54] METHOD OF PRODUCING BIODEGRADABLE PROSTHESIS AND PRODUCTS THEREFROM

[75] Inventors: Richard L. Dunn; Robert A. Casper, both of Birmingham, Ala.

[73] Assignee: Southern Research Institute, Birmingham, Ala.

[21] Appl. No.: 563,191

[22] Filed: Dec. 19, 1983

[51] Int. Cl.[4] .............................................. A61F 1/00
[52] U.S. Cl. ....................................... 623/16; 623/17; 623/18; 623/19; 623/20; 623/21; 623/22; 623/23; 128/92 YQ
[58] Field of Search ...................... 3/1, 1.9; 128/92 C, 128/92 G

[56] References Cited

U.S. PATENT DOCUMENTS

| | | | |
|---|---|---|---|
| 4,097,935 | 7/1978 | Jarcho | 3/1.9 |
| 4,131,597 | 12/1978 | Blüethgen | 3/1.9 |
| 4,192,021 | 3/1980 | Deibig et al. | 106/161 |
| 4,279,249 | 7/1981 | Vert et al. | 525/415 |
| 4,329,743 | 5/1982 | Alexander et al. | 3/1 |
| 4,356,572 | 11/1982 | Guillemin et al. | 3/1.9 |
| 4,411,027 | 10/1983 | Alexander et al. | 3/1 |
| 4,612,923 | 9/1986 | Kronenthal | 128/92 R |

*Primary Examiner*—John Kight
*Assistant Examiner*—Kriellion Morgan
*Attorney, Agent, or Firm*—Needle & Rosenberg

[57] ABSTRACT

Method of producing biodegradable prostheses comprising a composite of resorbable fibers reinforcing a biodegradable polymer matrix and the use thereof in medical applications such as bone plates and other orthopedic devices. The fibers include ceramic powders, $\beta$-TCP and CaAl and a biodegradable glass, CMP.

11 Claims, No Drawings

METHOD OF PRODUCING BIODEGRADABLE PROSTHESIS AND PRODUCTS THEREFROM

The government has rights in this invention pursuant to contract DAMD17-78-8059 awarded by the U.S. Army Institute of Dental Research, U.S. Army Medical Research and Development Command.

BACKGROUND OF THE INVENTION

The need for improved methods and materials to manage severe maxillofacial injuries is well recognized. In such cases, the surgeon faces the dual problem of restoring function and appearance. The patient suffering from an extensive maxillofacial injury is typically confronted with disfigurement, impaired speech, and eating difficulties as well as the psychological trauma resulting from the injury.

Ideally, fixation applicances should maintain the fractured bone segments in close approximation for the promotion of primary union and healing, provide sufficient strength and rigidity to prevent disruption of the primary union by external forces, and as the union becomes further ossified, transfer an increasing proportion of the external load to the healing bone so that it will be strained and exercised. The fulfillment of these criteria is necessary for the formation of healthy, hard tissue that has properties commensurate with those of virgin bone.

Implant materials used for such injuries over the years belong to three traditional classes: metals, ceramics, and polymers. The choice of material for the particular application depends on the type and magnitude of applied loads which the implant is expected to experience in vivo and whether the implant is to be a permanent or a temporary augmentation. When trying to make repairs to the skeletal system, surgeons and engineers must attempt to replicate the static and dynamic responses of bone. Bone consists of a framework of collagenous fibers, a mineral matrix consisting primarily of calcium hydroxyapatite, and a small amount of polysaccharides. Although bone is stronger and less deformable than polymeric materials, it is weaker than metals. Historically, metals have received wide application for the construction of devices for fixing fractures. Metals exhibit high values of tensile strength and compressive modulus; they can be fabricated into fixation hardware by a variety of conventional techniques; and they provide excellent resistance to the in vivo environment. Metals and alloys now used as surgical implants include 316 stainless steel, several cobalt-chromium alloys, titanium, zirconium alloys and tantalum.

In mandibular fracture repair, one of the major disadvantages with metal implants is atrophy of the healing bone as a result of the stress-protection effect of the rigid metal plate. Other drawbacks with metal fixation appliances are that they may cause local inflamation and may corrode with age.

Among the metallic materials, tantalum is superior in resistance to corrosion and has been extensively employed as fixation plates for fractured bones and as implants. The metal is, however, difficult to process. In contrast, ceramic materials show good affinity to bones often with bone tissue penetrating into the fine pores of the ceramic to produce a strong fixation. Bone and tissue compatibility with ceramics is excellent. The main disadvantage of ceramic materials is their poor impact strength as they are often brittle. This condition is quite evident with the more porous ceramics and leads to poor durability of ceramic implants and fixation devices. On the other hand, polymeric materials provide excellent impact strength, good biocompatibility, and they are easily molded to the desired shape; however, they do not possess the required strength and stiffness for bone fixation.

Those materials and many of the prior art materials suffer from the common drawback of being permanent. In many applications, such as a fixation appliance holding a fracture together while it heals, it is highly desirable if the implant can be resorbed by the body. Such an implant would biodegrade over a period of weeks or years, and be gradually replaced by natural bone growth. Such materials eliminate the need for a second surgery to remove the implant. However, homogenous fixation plates previously fabricated from biodegradable polymers have been shown to possess insufficient strength and rigidity for initial fracture fixation. Porous resorbable ceramics have also been used in bone repair, but they must be used in conjunction with other support because of their fragile nature.

The prior art includes U.S. Pat. No. 3,929,971 which discloses a synthetic material (either hydroxapatite or whitlockite) that may be used with other materials, such as organic polymers, to form a composite substance which could be useful in constructing a degradable prosthetic implant; U.S. Pat. No. 3,905,047 which discloses a biodegradable prosthesis containing an eutectic or metal pyrophosphate and high-modulus fibers formed of a refractory metal oxide; U.S. Pat. No. 4,330,514 is directed to a process for preparing a hydroxyapatite ceramic which is used in a nondegradable implant comprising the ceramic and an organic binding material; and U.S. Pat. No. 4,356,572 which is directed to a porous biodegradable bone implant which utilizes calcium carbonate in crystalline form.

SUMMARY OF THE INVENTION

The disadvantages of the prior art are overcome by the present invention comprising biodegradable, high-strength, rigid fixation systems formed of composites of biodegradable polymers reinforced with resorbable fibers, particularly calcium phosphate fibers; the degradation products of the composites of the present invention are nontoxic and harmless to the host. The preferred polymers include polyglycolide (PGA), poly(DL-lactide) (DL-PLA), poly(DL-lactide-co-glycolide) (DL-PLG), poly(L-lactide) (L-PLA), poly(L-lactide-co-glycolide) (L-PLG), polycaprolactone (PCL), polydioxanone, polyesteramides, copolyoxalates and the polycarbonates because of their degradation times and their degree of control of degradation.

The reinforcing fibers include the ceramic or the preferred glass forms of calcium phosphate. The ceramic fibers include those comprising $\beta$-tricalcium phosphate. These fibers may be prepared by wet-spinning mixtures of the powders with different polymeric binders, such as polyacrylonitrite (PAN-A), and solvents, such as dimethyl sulfoxide (DMSO). Ceramic loading, oxidative pretreatment, coupling agents and sintering conditions affect spinnability and fiber properties. Fibers of phosphate-free calcium aluminate (CaAl) produced by the same process may also be used although the resulting fibers are fragile and may fracture easily.

Due to the highly porous and fragile nature of the fibers produced from the ceramic powders, the preferred fibers of the present invention are glass fibers. Smooth, uniform fibers of calcium metaphosphate [Ca(PO$_3$)$_2$](CMP), a bioabsorbable glass, may be prepared by extruding or pulling filaments from a melt and air quenching. Fibers can also be prepared by the same process from a partially bioabsorbable glass composed of a mixture of silicon dioxide, sodium oxide, calcium oxide and phosphorous pentoxide.

It is preferred to use continuous filament fibers so that a high ratio of length to cross sectional area is obtained, the length to diameter or aspect ratio ranging from 10:1 to 1,000,000:1.

DETAILED DESCRIPTION OF THE ILLUSTRATIVE EMBODIMENT

The present invention relates to the incorporation of high-strength, high-modulus, biodegradable fibers in biodegradable polymers to form totally absorbable fracture-fixation plates or devices. The use of two bioabsorbable ceramic powders, $\beta$-TCP and CaAl, and a bioabsorbable glass, CMP, is described.

(A.)

Preparation of Ceramic Materials

Bone contains a matrix of calcium hydroxyapatite, a resorbable ceramic material, in callagen. The calcium hydroxyapatite provides rigidity and the same material, when incorporated into biodegradable polymers, should provide the necessary reinforcement for use as fixation plates or devices. A variety of ceramic forms of hydroxyapatite [Ca$_{10}$(PO$_4$)$_6$(OH)$_2$] and tricalcium phosphate [CA$_3$(PO$_4$)$_2$] have been reported in the literature. Recent evidence indicates that ceramic forms of hydroxyapatite are inert as implant materials while whose of tricalcium phosphate (Whitlockite) are bioabsorbable. The strength, durability, and absorption kinetics of tricalcium phosphate ceramics depend on the phasic nature of the final product, the lattice structure of the phases present, and the porosity and total surface area. Preparation of a calcium phosphate ceramic of high purity and single-phase nature is accomplished by the precipitation method of Salsbury and Doremus for production of $\beta$-Whitlockite ($\beta$-TCP), as follows:

A solution of calcium nitrate (1.40 moles) in 900 mL of distilled water is brought to pH 11 to 12 with concentrated ammonium hydroxide and thereafter diluted to 1800 mL. A solution of ammonium phosphate (1.00 moles) in 1500 mL distilled water is brought to pH 11 to 12 with concentrated ammonium hydroxide and thereafter diluted to 3200 mL to dissolve the resulting precipitate. The pH is again checked and additional concentrated ammonium hydroxide is added if necessary.

The calcium solution is vigorously stirred at room temperature, and the phosphate solution is added in drops over 30 to 40 minutes to produce a milky, somewhat gelatinous precipitate which is then stirred overnight (more than 12 hours). The reaction mixture is then centrifuged, and the clear supernatant fluid decanted. The resulting mineral sludge is homogeneously resuspended in distilled water to serve as a feedstock.

To produce green states which should afford 100% $\beta$-Whitlockite ceramics, aliquots of the feedstock are recentrifuged, homogeneously suspended in two volumes of dilute aqueous ammonium sulfate (1 to 2%) and then filtered on a Buchner funnel with application of mild suction and a rubber dam. After filtration for several hours, the compact clay-like cake is dried intact at 90° C. for 15 hours to produce directly the green state.

Sintering conditions, of course, may vary with the material and the phase or phases desired in the final product. For the production of $\beta$-Whitlockite, the green cake may be placed on an alumina dish and initially heated to 600° C. over 0.5 hours. The temperature is then raised quickly to 1150° C., the cake is sintered isothermally at 1150° C. for 1 hour, the temperature is reduced to 900° C., and the ceramic is cured at 900° C. for 4 hours.

Calcium aluminate is another resorbable ceramic material. Calcium aluminate of a 50:50 Ca/Al wt % composition [CaAl$_2$O$_4$] (CaAl) was 60% resorbed after one year implantation in monkeys. The Ca/Al ratio can be varied to produce several combinations of crystallographic phases and the various phases hydrolyze at varying rates providing a method for controlling the rate of ceramic dissolution. CaAl can be purchased from Pfaltz & Bauer, Inc., Samford, CT consisting of CaAl$_2$O$_4$ with quantities of Al$_2$O$_3$ and Ca$_{12}$Al$_{14}$O$_{22}$ as impurities.

(B.)

Preparation of Fine-Particle Sized Ceramic Powder

To prepare reinforcing ceramic fibers, especially with small diameters, it is necessary that the ceramic material consist of small particles. The small particles allow the extrusion of small-diameter ceramic filaments, and the finer particle size results in greater densification on sintering. Greater densification and the associated reduction in void volume of formed articles produces ceramic products, whether in pellet, rod or fiber form, with greater strength and structural rigidity. In addition, the breaking strength of sintered ceramic fibers is usually inversely proportional to the diameter of the fiber; thus, the smaller the fiber, the stronger it is per unit size. The same relationship has been found with sintered TCP fibers.

One method to reduce the ceramic powder to small particles is the use of a Megapack high-energy vibratory mill. The system employs the use of small-diameter steel balls vibrating at high frequencies for grinding of ceramic powders. The procedure used to grind ceramic samples to fine particle sizes with this mill is as follows: A slurry of TCP (or phosphate-free CaAl) in water was added to the vibratory mill, and the mill was activated and allowed to run for 4 hours. During that time, samples were taken at periodic intervals and examined by scanning electron microscopy (SEM) to determine particle-size range. A milling time of 4 hours was found to be sufficient to yield particles in the 1- to 2-$\mu$m range. At the end of that time, the slurry was removed from the mill and centrifuged for 30 minutes at 100 g. The supernatant was decanted and dimethyl acetamide was added to the centrifuge bottle; the contents were then agitated to resuspend the compacted ceramic powder. This process was repeated several times until all of the water was replaced by dimethyl acetamide.

The vibratory milling technique allowed preparation of slurries of ceramic powder in the appropriate polymer solvent both effectively and efficiently. Ceramic particles in this size range were appropriate for use in the wet-spinning of fine diameter filaments.

(C.)

Wet-Spinning of Ceramic Fibers Using Polymeric Binders

Of the number of methods for use in the production of ceramic fibers examined, fiber production by wet-spinning appears to be the most successful method. Simplistically speaking, fiber production by wet-spinning involves extruding a mixture of ceramic powder, binder (PAN-A), and solvent (DMSO) into a trough or bath containing a non-solvent for the binder. During extrusion into the non-solvent bath, the mixture coagulates to form a fiber or filament. For success in making fibers by wet spinning, the solvent for the binder must be soluble in the coagulating bath, which must be a non-solvent for the binder.

The fibers or filaments are subsequently drawn from the coagulating bath using a series of water-flushed, heated godets to rinse and evaporate the remaining solvent. After passing through the rinsing and drying system, the fibers are taken up on a winding reel. The collected fibers are then soaked in distilled water to assure complete solvent removal and are, thereafter, dried in an air-circulating oven to produce the final dried fiber. For the production of fibers from both $\beta$-TCP and phosphate-free CaAl, it is necessary to sinter the dried fibers in an inert atmosphere (nitrogen) maintained above 1150° C. to achieve coalesence and densification of the ceramic particles.

1. Polymeric Binders

As a consequence of the elevated temperature required for proper sintering of both $\beta$-TCP and phosphate-free CaAl, polymeric binders with superior thermal stability are required for use in the wet-spinning process. Although no resin yet produced is capable of withstanding these temperatures, three highly thermally stable resins were examined to see if they might effectively bind the ceramic powders together in fiber form until preliminary sintering (lower temperature) was achieved. These binders were Barex 210 (Vistron Corp., Chemicals Division, Cleveland, OH), a terpolymer mostly composed of acrylonitrile; Polyacrylonitrile Type A (PAN-A) (Du Pont, Wilmington, DE); and Ethocel #1 Standard (Dow Chemical Co., Midland, MI), an ethylcellulose material.

The thermal stability of PAN-A and, hence, the spun fiber, may be enhanced by subjecting the material to an oxidative pretreatment. The pretreatment improves thermal stability by forming a ladder polymer. Ethyl cellulose offered similar thermal stability without the necessity of a pretreatment step, although the fibers prepared with ethyl cellulose are inferior to those with PAN-A as a binder.

2. Dispersing agents

In wet spinning of ceramic fibers, dispersing agents are often used to prevent clumping of the ceramic particles and plugging of the in-line filter screen. Nuosperse, obtained from Tenneco Chemicals (Piscataway, NJ) is more compatible with the spinning solvent, DMSO, than Tamol 960 and Tamol SN from Rohm and Haas (Philadelphia, PA). It was successful in preventing clumping of the ceramic particles, and its addition to the spinning dope improved the spinnability of the ceramic materials.

3. $\beta$-TCP fibers

TCP powder prepared as described previously was wet sieved using No. 60 (250-$\mu$m) and No. 140 (160-$\mu$m) sieves. The fine particle cut was used to make the spinning dope. TCP was mixed with a solution of PAN-A in DMSO to make up the spinning composition. Care was taken to remove any entrapped air bubbles. The final spinning dope consisted of 7.4% TCP, 1.8% PAN-A, and 90.8% DMSO on a weight basis.

Fibers were prepared by wet extrusion using a hypodermic syringe and hypodermic needles of various sizes. The needles ranged from 15 G (1.37 mm ID) to 27 G (0.2 mm ID). Distilled water at room temperature was used as the coagulating medium. The spinning dope was loaded into the syringe barrel, and the tip of the needle was placed below the surface of the coagulating fluid. Pressure was applied until a bead of coagulum formed at the needle's tip. The bead was grasped with a pair of tweezers and pressure was reapplied to the syringe barrel. Fibers were extruded for the length of the coagulating bath. Fibers prepared using the smaller diameter needles were considerably more difficult to extrude than fibers prepared using the larger needles. The extruded fibers were removed from the coagulating bath and placed in another water bath and allowed to soak to remove solvent. After soaking for a sufficient time, the fibers were removed from the bath with tweezers and placed on Teflon sheeting to dry in air overnight. The smaller fibers were easier to handle and exhibited more structural integrity. This was probably due to a higher residual solvent content in the larger fibers.

$\beta$-TCP fibers were also prepared on wet-spinning equipment designed for production of rayon fibers. A spinning dope consisting of 10% $\beta$-TCP, 15% Barex 210 acrylic polymer, and 75% N,N-dimethylacetamide was loaded into a cylindrical, stainless steel feed pot. The feed pot was pressurized with compressed air (20 psi), and the spinning dope was forced from the feed pot through stainless steel tubing (0.25-in.-OD, type 304) to a Zenith gear pump driven by a Zenith Model QM drive motor. The Zenith pump delivered the spinning dope (at 0.29 cm$^3$ per revolution; 1.45 cm$^3$/min) to a spinneret with an orafice diameter of 0.020 in. The spinneret was submerged in a water bath. As the spinning dope came in contact with the water, it coagulated to form a fiber. After traversing the coagulation bath (18 in.), the fiber was taken up by the first godet. This godet (80 ft/min surface speed; 107° F.) was equipped with a tap water spray to remove solvent from the fiber. The fiber was then taken up on a second heated godet (84 ft/min surface speed; 97° F.) and rinsed with a warm water spray. The fiber was passed around a third heated godet (87 ft/min surface speed; 105° F.) and collected on a Leesona Model 955 take-up winder.

The fibers were then subjected to oxidative pretreatment to promote the formation of a ladder polymer and enhance the thermal stability of the binder matrix. Pretreatment was accomplished by placing the fibers in an air-circulating oven maintained at 200° C. for 30 minutes. Pyrex test tubes were used to contain the fibers during the pretreatment process. The fibers changed from white to tan during pretreatment.

After pretreatment, the fibers were sintered in a Lindberg Hevi-Duty SB oven. The oven was maintained at 1200° C. and purged with nitrogen for the duration of the sintering cycle. The sintered fibers were light yellow. After sintering, some of the fibers shrank to less than 40% of their original diameter.

The fibers were tested for breaking strength on an Instron Model TMS Serial 72 testing machine. The fibers were prepared for testing by mounting on cardboard tabs. The finest fibers were attached to the tabs with paraffin, and the larger fibers were attached with sealing wax. Samples were pulled at a rate of 1 in./min. until fracture occurred and the force at break was determined. After being tested, the samples were removed from the Instron, the diameter at the fracture point was determined with a micrometer and used to calculate the breaking strength in terms of force per unit area. The fracture surfaces were then examined by SEM. The test results are presented in the following table:

| BREAKING STRENGTH OF TRICALCIUM PHOSPHATE FIBERS | |
|---|---|
| Average diameter mm | Breaking strength psi |
| 0.559 | 169 |
| 0.508 | 353 |
| 0.356 | 69 |
| 0.124 | 419 |
| 0.122 | 477 |
| 0.074 | 1607 |

There is a dramatic effect of fiber diameter on tensile strength. As fiber diameter decreases, the strength increases. Such behavior is commonly found in the preparation of ceramic fibers. Results shown in the table reflect the average of test results for five specimens of each fiber diameter. One sample of the smallest diameter fiber had a tensile strength of 2500 psi. SEM photos showed voids and irregularities at the fracture surface of all specimens. In general, larger voids were associated with lower breaking strength, reflecting the stress-concentrating effects of the irregularities.

4. CaAl fibers

Fibers of phosphate-free calcium aluminate were prepared following the procedures used for $\beta$-TCP fiber production and using the same solvent and binder. After sintering, the fibers were quite fragile.

Calcium aluminate (Pfaltz & Bauer, Inc., Stamford, CT) was used to prepare the fibers. X-ray diffraction analysis revealed that the powder consisted of $CaAl_2O_4$ but also contained significant amounts of $Al_2O_3$ and $Ca_{12}Al_{14}O_{22}$. The CaAl was dry sieved through a No. 100 sieve (150-$\mu$m) to break up any clumps and remove any large particles.

The spinning dope had a ceramic-to-binder ratio of 80:20 and consisted by weight of 25% CaAl, 6% PAN-A, and 69% DMSO. Fibers were extruded from a hypodermic syringe and needle, as were the TCP fibers. Needle sizes 15 G through 25 G were used to form fibers. The 27 G needle proved to be too fine for the CaAl dope. The fibers were coagulated in a tap-water bath at ambient temperatures. The coagulated fibers were quite rigid and easier to handle than the TCP fibers at this stage. CaAl fibers were also prepared by the pilot-scale equipment used for the $\beta$-TCP fiber production. A 70:30 by wt blend of CaAl and Barex 210 in a suspension in N,N-dimethylacetamide was extruded at a rate of 1.75 cm$^3$/min into tap water at 70° F. The first and second godets were operating at a speed of 94 ft/min and the third godet at a speed of 96 ft/min. The temperatures were 110°, 115°, and 115° F. for the three godets respectively. The fibers were dried at ambient conditions overnight. Oxidative pretreatment was performed in a circulating-air oven at 200° C. for 30 minutes. Prior to oxidation the fibers were white. After oxidation the fibers turned brown. The fibers were then placed in an oven under a nitrogen purge, heated at 1200° C., held for 1 hour, and allowed to cool overnight. When the fibers were removed from the oven, they were found to be extremely fragile.

(D.)

Fiber Production From Biodegradable Glasses

Although sintering of ceramic particles produces bioabsorbable ceramic fibers, the voids still present in the fibers cause them to be somewhat fragile and weak. A void-free ceramic fiber produced by melting and extrusion of a bioabsorbable glass gives a stronger and more durable fiber for use in polymer reinforcement. Glasses are converted to fibers by drawing fibers from hot melts. The high surface tension and slow rate of change of viscosity with temperature of melted glass permits formation of stable meniscuses and enables fibers to be formed and drawn from a suitable crucible after the natural flow of molten glass downward by gravity. Both marble melt and direct melt processes are used to produce glass fibers.

1. Bioglass fibers

Bioglass is a partially biodegradable glass composed of 45% silicon dioxide, and various metallic oxides (sodium oxide, calcium oxide and phosphorous pentoxide). Only the silicon dioxide portion of the glass is non-absorbable.

Fibers were prepared from the Bioglass by heating the material in a crucible until it became molten (900° C.) and withdrawing filaments with a stainless steel rod. Fibers were produced by this procedure, but there was considerable variation in both fiber diameter from sample to sample and uniformity of diameter throughout the length of a given sample. Samples of the glass fibers were mounted and tested in the same manner as the ceramic fibers. Breaking strength of the glass fibers varied from 9000 to 50,000 psi. This variation was to be expected in view of the lack of uniformity from one sample to the next. However, the formation of fibers with high tensile strengths was evident.

Fibers prepared in the fashion described above were tested for bioabsorption. Samples of the fibers were cut into 2-in. lengths for breaking-strength determination, and the 2-in. lengths were weighed. Some fibers were mounted and broken to determine initial breaking strength. Their average initial breaking strength was about 45,000 psi, and their average diameter was 0.026 mm. The remaining fibers were placed in phosphate-buffered saline at a pH of 7.2 in a 37° C. oven for 18 days. The fibers were then removed from the saline, dried, reweighed, and broken to determine final breaking strength. Their average weight loss was about 5%, and their average breaking strength was less than 200 psi.

2. CMP fibers

CMP is known as a hydrolytically unstable glass. Consisting of calcium and phosphorous, it degrades within the body to harmless components of normal body fluid. CMP, however, must be properly purified before it can be spun into fibers for use in reinforcing biodegradable polymers. Following the procedure given in U.S. Pat. No. 4,049,779, CMP of sufficient purity for fiber formation is obtained. One liter of a 3-molar solution of phosphoric acid was prepared. One hundred grams of $CaCo_3$ was then slowly dissolved in the acid solution. Impurities were removed by precipitating with 2.5 g of ammonium 1-pyrrolidine dithiocarbamate dissolved in 50 mL of water. The resulting grey precipitate was then removed by filtration. The supernatant was concentrated by evaporation, and the pure CMP was precipitated. The precipitate was filtered and washed with acetone to remove any residual phosphoric acid. The white material was then placed in an alumina dish and baked in an oven at 600° C. for 24 hours, 800° C. for 72 hours, and cooled slowly to room temperature. The baking steps allow the CMP salt to be chemically condensed and polymerized to produce the CMP glass.

The resulting grey, foamed, brick-like substance is then placed in an alumina or platinum crucible, heated in an oven at 600° C. for 2 hours, at 800° C. for 16 hours, and at 1000° C. for 2 hours, after which time the crucible is removed from the oven and transferred to the fiber-drawing apparatus. This equipment consists of an oxygen/natural gas heating source for the crucible and a 3.75 in. -OD stainless steel take-up spool for drawing the fibers. The speed of the spool can be controlled to produce fibers with the desired diameters. A typical draw speed of 7.2 in./sec. is used. The spool is also heated with a natural gas flame. By inserting the tip of a stainless steel rod into the molten glass, a fiber can be drawn from the melt and passed around the take-up spool. If the melt is maintained at the proper temperature ($\simeq 1000°$ C.), a very fine glass fiber can be wound on the take-up spool. The resulting fibers have good strength and uniformity. A typical fiber has a tensile strength of approximately 51,000–110,000 psi, an initial modulus of $5 \times 10^6$ psi, a diameter of about 5 mils, and a density of 2.67 g/cm$^3$. These properties are comparable to commercial glass fibers.

In vitro studies of the CMP fibers in 0.9% USP saline at 37° C. show the fiber begins to dissolve from the surface after only 10 days, and they are completely dissolved after 30 days.

(D.)

Biodegradable Composites

For the high-strength, high-modulus, bioabsorbable ceramic or glass fibers to be useful, they must be incorporated into a biodegradable polymer matrix. The matrix protects the fibers from abrasion and breakage, and they provide a structure for bone-fixation plates. The fibers in return provide the structural rigidity needed for the polymer plate or device to maintain support.

1. Biodegradable Polymers

The following polymers (with their approximate degradation times) are all candidates for the biodegradable composite of the present invention. These polymers are all biodegradable to water-soluble, nontoxic materials which can be eliminated from the body. All are well known for use in humans and their safety has been demonstrated and approved by the FDA. Although these polymers are normally linear, crosslinked resins can be prepared from these materials by those skilled in the art, and these materials are also included as suitable biodegradable polymer matrices.

| Polymer | Degradation Time, Months |
|---|---|
| Polycaprolactone | 24–36 |
| Poly(L-lactide) | 24 |
| Poly(DL-lactide) | 12–18 |
| Polyglycolide | 3–4 |
| 95:5 Poly(DL-lactide-co-glycolide) | 12 |
| 90:10 Poly(DL-lactide-co-glycolide) | 10 |
| 85:15 Poly(DL-lactide-co-glycolide) | 9 |
| 75:25 Poly(DL-lactide-co-glycolide) | 5 |
| 50:50 Poly(DL-lactide-co-glycolide) | 2 |
| 90:10 Poly(DL-lactide-co-caprolactone) | 9 |
| 75:25 Poly(DL-lactide-co-caprolactone) | 6 |
| 50:50 Poly(DL-lactide-co-caprolactone) | 2 |
| Polydioxanone | 12 |
| Polyesteramides | 4–12 |
| Copolyoxalates | 4–12 |
| Polycarbonates | 2–12 |
| Poly(glutamic-co-leucine) | 24–48 |

The preferred polymers are the poly(DL-lactide-co-glycolide) materials because of the degradation times and their degree of control of degradation. The poly(L-lactide-co-glycolide) materials not mentioned in the table should give similar results. Poly(DL-lactide) is also preferred as are the polydioxanone, polyesteramides, copolyoxalates and the polycarbonates. Polycaprolactone, poly(L-lactide), and the poly(glutamic-co-leucine) are less preferred because of their long degradation times.

With a composite formed from a biodegradable polymer and resorbable fibers, the strength decreases with resorption time within the body. This decrease in strength is important because the fixation plate transfers the load with time to the healing bone and prevents stress protection atrophy. The loss of strength of the polymer plates reinforced with biodegradable fibers will depend primarily upon the degradation rate of the polymer because the polymer completely encases the fibers. The degradation rate of the polymeric matrix depends upon the type of polymer used. It should be noted that the degradation times set forth above are for complete disappearance from the polymer. The time for strength loss in the composite will be considerably less and can be approximated as one half the total polymer degradation time. Composites which lose their strength in one month will be useful as well as those that last up to about one year. The preferred times will be three to six months. It should also be noted that the biodegradation times of the polymers and the corresponding strength losses of the composites will depend upon polymer molecular weights. The values given in the table are for normal molecular weights. Higher molecular weight polymers will last longer and those lower in molecular weight will degrade faster. The degradation rate of the polymer can be changed by control of molecular weight, by the type of biodegradable polymer, and by controlling the ratio of lactide to glycolide in copolymers.

2. Reinforcing Fibers

The term "fiber" as used herein is defined as any material that has a high ratio of length to cross sectional area with minimums suggested as 10:1 to 100:1, and a maximum cross sectional area of $7.85 \times 10^{-5}$ in.$^2$ and a maximum transverse dimension of 0.010 in. With continuous filament fibers which are preferred, the length to diameter (aspect ratio) is maximized to give the best reinforcement. However, the composites can be made with chopped or shorter lengths of fibers. With these, the aspect ratio is lower and the level of reinforcement is less. Thus, the aspect ratio can range from 10:1 up to really high numbers such as 1,000,000:1. The preferred range is 100:1 to 1,000,000:1.

3. Composite Fabrication

The fibers can be incorporated into the polymer matrices by several methods. In one approach, the fibers can be chopped into small pieces, mixed with the molten polymer, and formed into the desired shape by injection molding, compression molding, or extrusion. In another procedure, the chopped fibers can be mixed with a solution of the polymer and the mixture cast into a film with evaporation of the solvent. The films can then be laminated or molded to the desired shape. The preferred method, however, is to use continuous filaments of the fiber to provide maximum strength and regidity. Therefore, the ceramic or glass fibers are wrapped around a Mylar- or Teflon-coated mandril and dipped into or sprayed with a solution of the polymer in a suitable solvent. The solvent is evaporated, and the dipping or spraying repeated to obtain a composite film of the desired thickness. The film is then removed from the mandril, and pressed under pressure and heat to provide flat, bubble-free sheets. These sheets are then laminated with other sheets of the same composition or with polymer sheets containing no fibers to produce the fixation plate.

As an example, films of DL-PLA were prepared from purified polymers having inherent viscosities from 0.58 dL/g to 1.27 dL/g measured in chloroform at 30° C. Either ceramic or glass fibers are wrapped around a Mylar-coated mandril and sprayed with a solution of the same DL-PLA in p-dioxane. After the solvent evaporates, the spraying is then repeated to obtain a composite film of the desired thickness. When the appropriate thickness is obtained, the film is removed from the mandril, cut, and pressed with a hydraulic press maintained at 70° C. and 29,000 psi to provide flat, bubble-free sheets. These sheets are then laminated with sheets of the same polymer containing no fibers to produce a plate. Five sheets of fiber-reinforced material are combined with four sheets of polymer.

In another procedure, a hot-pressed film of PLA is placed in a mold and the film is brushed with solvent until it is tacky. Then a layer of the CMP fiber is placed lengthwise along the film taking care not to overlap the fibers which causes breakage. Additional solvent is then brushed over the fiber and another polymer film is placed over the fibers to which it readily adheres. The top of the new film is then wetted, more CMP fibers placed onto it, and the process repeated until 6 layers of fiber are laminated between 7 layers of film to give a composite with 40% by volume of CMP fiber. The solvent is allowed to dry completely, and the laminate is heat-pressed at 60° C. and 20,000 psi for 15 minutes. This gives better lamination of the films and removes any residual solvent bubbles.

The plates produced by this procedure were evaluated in three-point bending tests (ASTM D790). Flexural strengths of 6,000–10,000 psi and flexural moduli of about $1\times 10^6$ psi were found. These compare favorably with those values obtained for nonbiodegradable polymer/fiber composites, and they show the improvements over non-reinforced biodegradable polymer plates.

| Materials | Flexural Strength, psi | Flexural Modulus, psi |
|---|---|---|
| Bone | 10,000–20,000 | 1 to 3 $\times 10^6$ |
| Steel | 75,000 | 30 $\times 10^6$ |
| DL-PLA | 2,000–4,000 | 0.3 $\times 10^6$ |
| Carbon-reinforced DL-PLA | 20,000–40,000 | 1 to 4 $\times 10^6$ |
| CMP-reinforced DL-PLA | 6,000–10,000 | 1 $\times 10^6$ |

4. Solvents for Biodegradable Polymers

The following table sets forth what solvent(s) will dissolve the biodegradable polymers useful in the present invention:

| Polymers | Solvent |
|---|---|
| Polycaprolactone 90:10 poly(DL-lactide-co-caprolactone) 75:25 poly(DL-lactide-co-caprolactone) 50:50 poly(DL-lactide-co-caprolactone) poly(DL-lactide) 95:5 poly(DL-lactide-co-glycolide) 90:10 poly(DL-lactide-co-glycolide) 85:15 poly(DL-lactide-co-glycolide) | dichloromethane, chloroform, toluene xylene, p-dioxane, and THF. |
| 50:50 poly(DL-lactide-co-glycolide) | HFIP (hexafluoroisopropanol) and HFASH (hexafluoroacetone-sesquihydrate) |
| polydixanone | tetrachloroethane and chloroform |
| polyesteramides | cresol |
| copolyoxalates | chloroform |
| polycarbonates | ketones, esters and partially chlorinated hydrocarbons |
| poly(glutamic-co-leucine) | benzene |

What we claim is:

1. A method of producing a totally biodegradable prosthesis or implant comprising the steps of
   (a) encasing an effective amount of fibers selected from the group consisting of calcium phosphate, and calcium aluminate in a matrix of a polymer selected from the group consisting of polyglycolide, poly(DL-lactide), poly(L-lactide), polycaprolactone, polydioxanone, polyesteramides, copolyoxalates, polycarbonate, poly(glutamic-co-leucine) and blends, copolymers and terpolymers thereof to form a composite; and
   (b) forming said composite to the desired shape.

2. A method as defined in claim 1 wherein said calcium phosphate fibers are comprised of β-tricalcium phosphate.

3. A method as defined in claim 1 wherein said calcium phosphate fibers are comprised of calcium metaphosphate.

4. A method a defined in claim 1 wherein said effective amount ranges from 10–90% by volume.

5. A method as defined in claim 1 wherein said effective amount is preferably 30–80% by volume.

6. A method as defined in claim 1 wherein the aspect ratio of said fibers ranges from 10:1 to 1,000,000:1.

7. A biodegradable prosthesis or implant, comprising
   (a) a matrix formed from a polymer selected from the group consisting of polyglycolide, poly(DL-lactide), poly(L-lactide), polycaprolactone, polydioxanone, polyesteramides, copolyoxalates, polycarbonate, poly(glutamic-co-leucine) and blends, copolymers and terpolymers thereof; and
   (b) fibers selected from the group consisting of calcium phosphate and calcium aluminate incorporated within said matrix in an amount ranging from 10–90% by volume and said fibers having an aspect ratio of 10:1 to 1,000,000:1.

8. A biodegradable prosthesis or implant as defined in claim 7 wherein said matrix is a film of said polymer and said prosthesis or implant comprises a predetermined number of alternating layers of said film and said fibers.

9. A method of repairing fractured bone segments in animals, comprising the step of surgically implanting adjacent said bone segments a prosthesis or implant formed of a composite of fibers selected from the group consisting of calcium phosphate and calcium aluminate, said fibers reinforcing a matrix formed from a polymer selected from the group consisting of polyglycolide, poly(DL-lactide), poly(L-lactide), polycaprolactone, polydioxanone, polyesteramides, copolyoxalates, polycarbonate, poly(glutamic-co-leucine) and blends, copolymers and terpolymers thereof.

10. A method of producing a totally biodegradable composite material for prosthetic and implant devices, comprising the step of encasing an effective amount of a reinforcing material in the form of fibers selected from the group consisting of calcium phosphate and calcium aluminate in a matrix of a polymer selected from the group consisting of polyglycolide, poly(DL-lactide), poly(L-lactide), polycaprolactone, polydioxanone, polyesteramides, copolyoxalates, polycarbonate, poly(glutamic-co-leucine) and blends, copolymers and terpolymers thereof.

11. A totally biodegradable composite material for prosthetic and implant devices, comprising:
  (a) from 10–90% by volume of a reinforcing material in the form of fibers selected from the group consisting of calcium phosphate and calcium aluminate; and
  (b) a polymer encasing said reinforcing material, said polymer being selected from the group consisting of polyglycolide, poly(DL-lactide), poly(L-lactide), polycaprolactone, polydioxanone, polyesteramides, copolyoxalates, polycarbonate, poly(glutamic-co-leucine) and blends, copolymers and terpolymers thereof.

* * * * *